US008142390B2

(12) United States Patent
Birmelin et al.

(10) Patent No.: US 8,142,390 B2
(45) Date of Patent: Mar. 27, 2012

(54) SYRINGE DEVICE WITH AN ELONGATE PLUNGER SPACE

(75) Inventors: Uwe Birmelin, Hügelheim (DE); Martin Eberl-Lang, München (DE)

(73) Assignee: Rexam Pharma GmbH, Neuenburg (DE)

( * ) Notice: Subject to any disclaimer, the term of this patent is extended or adjusted under 35 U.S.C. 154(b) by 0 days.

(21) Appl. No.: 12/599,363

(22) PCT Filed: Dec. 3, 2007

(86) PCT No.: PCT/EP2007/010492
§ 371 (c)(1),
(2), (4) Date: Apr. 20, 2010

(87) PCT Pub. No.: WO2008/135074
PCT Pub. Date: Nov. 13, 2008

(65) Prior Publication Data
US 2010/0256555 A1 Oct. 7, 2010

(30) Foreign Application Priority Data
May 7, 2007 (DE) .......................... 10 2007 021 243

(51) Int. Cl.
*A61M 31/00* (2006.01)
*A61M 5/00* (2006.01)
(52) U.S. Cl. .......................................... 604/60; 604/208
(58) Field of Classification Search .................. 604/208, 604/210, 220–222, 60, 224
See application file for complete search history.

(56) References Cited

U.S. PATENT DOCUMENTS

| 2,648,334 | A | * | 8/1953 | Brown et al. | 604/205 |
| 5,328,476 | A | * | 7/1994 | Bidwell | 604/110 |
| 5,344,409 | A | * | 9/1994 | Ennis et al. | 604/210 |
| 5,370,628 | A | | 12/1994 | Allison et al. | |
| 5,382,476 | A | * | 1/1995 | Weiser et al. | 428/411.1 |
| 2005/0131354 | A1 | * | 6/2005 | Tachikawa et al. | 604/187 |
| 2009/0131864 | A1 | * | 5/2009 | Pickhard | 604/83 |

FOREIGN PATENT DOCUMENTS

| EP | 0292936 | 11/1988 |
| EP | 0564038 | 10/1993 |
| EP | 1323450 | 9/2004 |
| EP | 1323450 B1 * | 9/2004 |
| WO | WO 2006045132 A2 * | 5/2006 |

* cited by examiner

*Primary Examiner* — Nicholas Lucchesi
*Assistant Examiner* — Jenna Zhang
(74) *Attorney, Agent, or Firm* — Volpe and Koenig, P.C.

(57) ABSTRACT

A syringe device (1) with an elongate plunger space (2), a receiving chamber (3) for receiving solid medicaments (4), and a hollow needle (5) arranged in the plunger space (2), and also a plunger (7) which is suitable for movement in the plunger space (2) and bears a ram (8) for pushing out the solid medicament (4). For displacement of the plunger (7) there is a plunger rod (9) which acts thereon and, for its use, can be extended telescopically out of the plunger space (2) and relative to the plunger (7) and can be coupled to the plunger by means of a lock (10). The locking of the plunger (7) to the plunger space (2) is opened or released only by complete withdrawal of the plunger rod (9) in its operative position while at the same time the plunger rod (9) is coupled to the plunger (7) in this position in the pushing direction such that the medicament can then be pushed out.

8 Claims, 4 Drawing Sheets

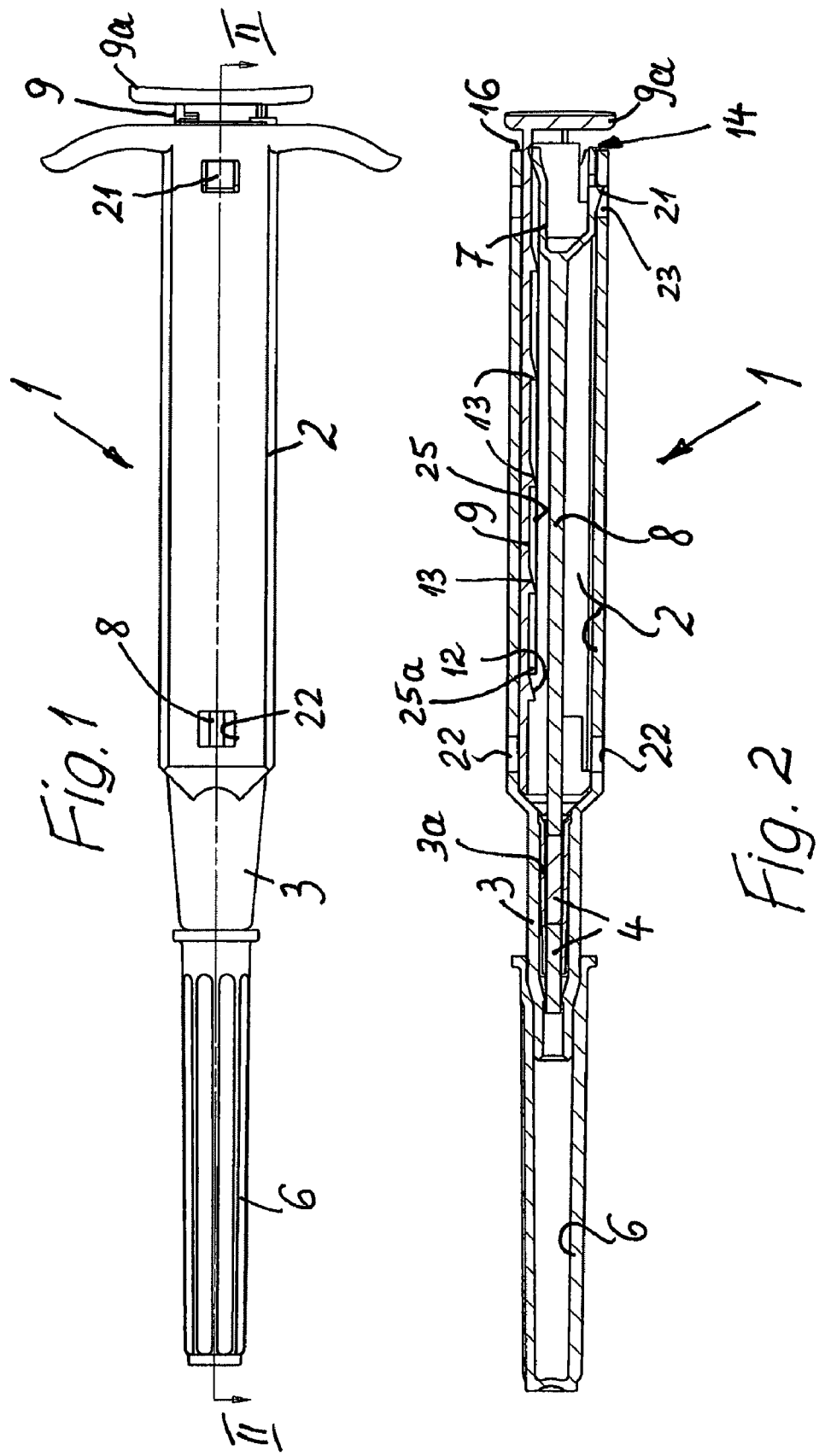

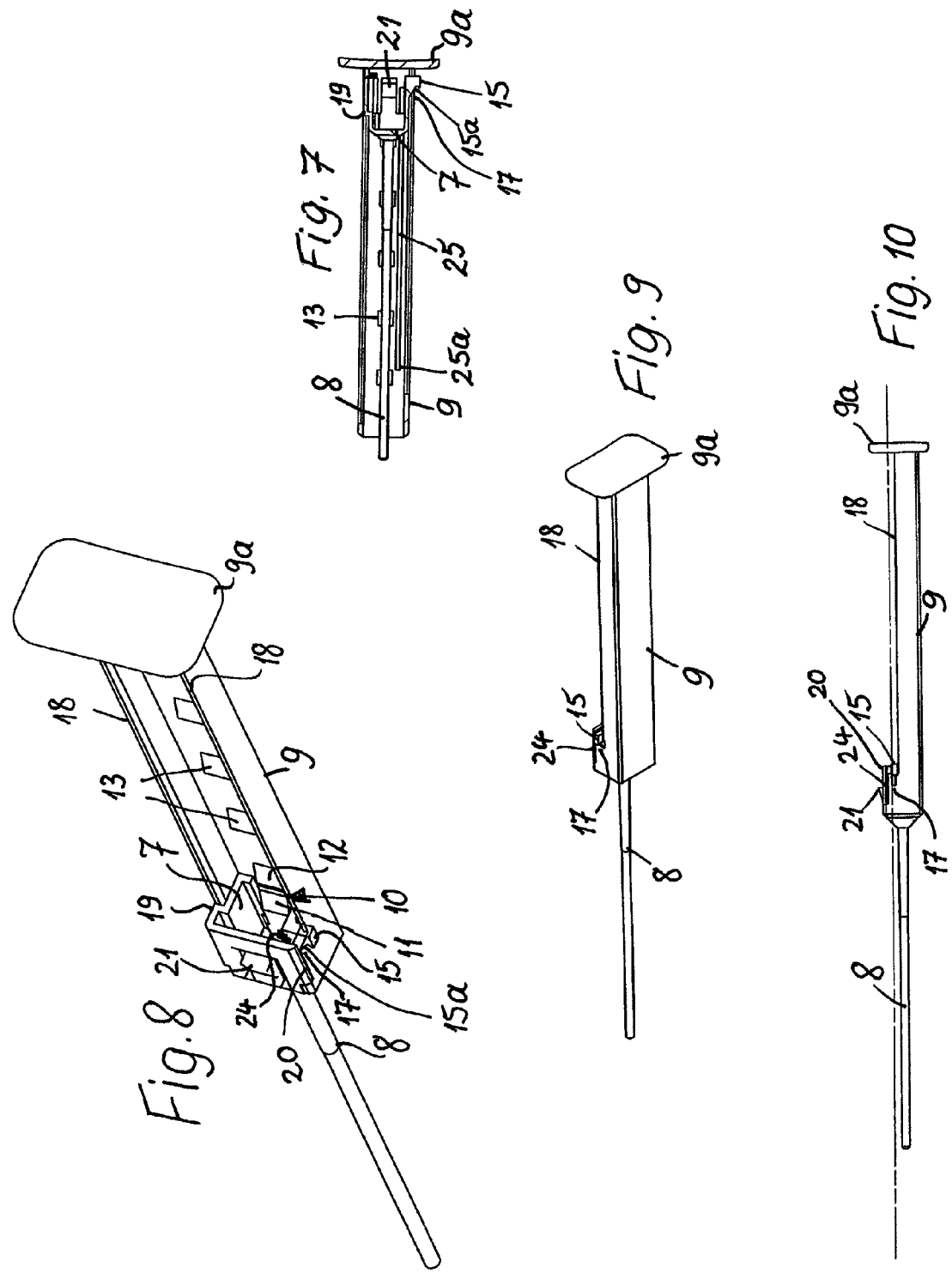

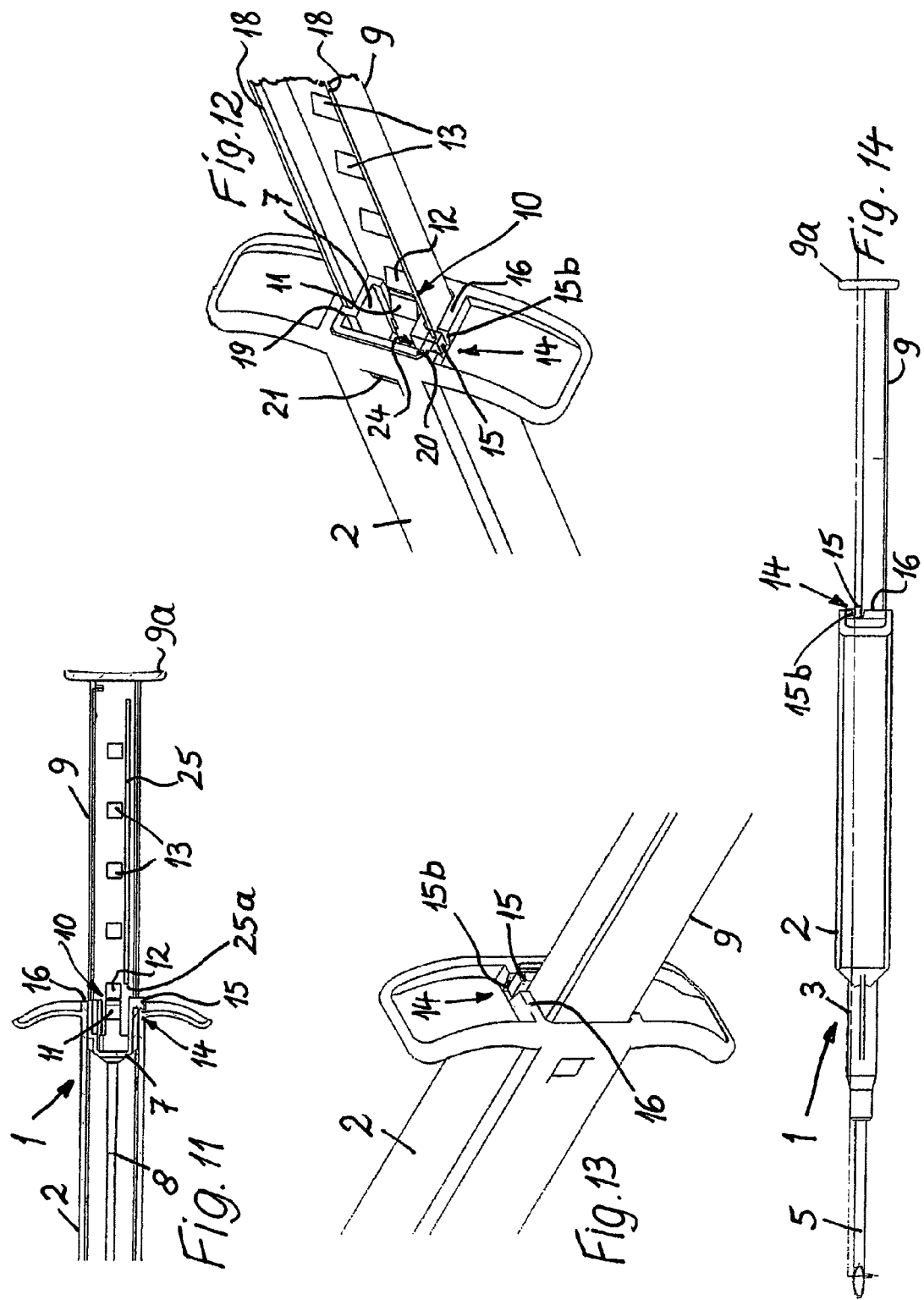

SYRINGE DEVICE WITH AN ELONGATE PLUNGER SPACE

CROSS-REFERENCE TO RELATED APPLICATIONS

The present application is a United States National Stage application of International Application No. PCT/EP2007/010492, filed on Dec. 3, 2007, and claims the benefit of German Patent Appln. No. 102007021243.9, filed on May 7, 2007, the entire contents of both of which are herein incorporated by reference.

BACKGROUND

The invention relates to a syringe device comprising an elongated plunger space or cylinder, having a receiving chamber for receiving one or more solid medicaments, having a hollow needle arranged at the plunger space, and having a plunger suitable for displacement in the plunger space or cylinder, comprising a ram for pushing the solid medicament through and out of the hollow needle, with a plunger rod engaging the plunger that can be telescopically extended for use and/or can be retracted in reference to the plunger against its direction of operation and can be coupled to the plunger by way of a lock.

Such a syringe device is known from EP 1 323 450 B1 and has proven useful. The entire syringe device is initially very compact and its important parts are largely located inside the housing-like plunger space protected thereby and secured from damage. When the plunger rod that can be telescopically retracted is pulled out of the plunger space it is displaced in reference to the plunger until it reaches a locking or coupling position said the plunger such that thereafter any insertion of the plunger rod also displaces the plunger and thus the solid medicament, initially held in a clamped sheath, is moved out of said sheath and out of the receiving chamber and is moved through the hollow needle and ultimately applied.

The handling of said syringe device has shown that during its use it may perhaps be forgotten to actually retract the telescopically retractable plunger rod to such an extent that it reaches the locking position with the plunger, so that in a subsequent insertion of the plunger rod no application of the medicament occurs or only an insufficient one.

SUMMARY

The object is therefore to provide a syringe device of the type defined at the outset, by which any faulty operation or faulty application can be largely prevented.

In order to attain this object, the syringe device of the type defined at the outset is characterized in that the parts or sections of the plunger telescopically adjustable in reference to each other and the plunger rod may comprise at least one or more mutual locks for intermediate positions of the plunger rod that can be telescopically retracted in reference to the plunger, which locks prevent any displacement in the direction of application when the plunger rod is only partially retracted in reference to the plunger space, and with in the initial position a coupling or locking of the plunger is provided when it is in its initial position, which can be released by the plunger rod when retracted to its operational position, in which the plunger rod is connected to the plunger in the pushing direction.

When in such a device the plunger rod is insufficiently retracted to reach the necessary operational position at the plunger, it cannot be displaced in the direction of application due to the lock, so that the user can only displace the plunger in the operational direction if he/she further retracts the plunger rod until it has actually reached its final position and thus the coupling position to the plunger and then the plunger is unlocked in reference to the plunger space or housing. Due to the fact that any displacement of the plunger rod in the direction of application is blocked at an insufficient retraction the user notices that he/she has not reached the operational position so that it can be avoided that an insufficient application or none at all occurs by displacing the plunger rod out of its intermediate position. Therefore, the blockage of the plunger rod in intermediate positions against the pushing direction occurs via the snapping connection to the plunger, which in turn is coupled in a form-fitting manner to the plunger space such that only after the complete retraction of the plunger rod and the consequently simultaneous release of the plunger, the application can occur in the desired fashion.

A protrusion, elastic or adjustable into the contour of the plunger, may be provided at the plunger, which in an initial position, with the plunger being retracted, automatically engages a coupling recess at a coupling site of the plunger space. This prevents the possibility that the plunger can be displaced from its initial position before the coupling has been released by the retracted plunger rod.

The protrusion, arranged at the plunger and automatically adjustable in the coupling position, may represent a snapping or locking latch, in the coupling position engaging below a position of the plunger space or its housing. This way, in the coupling position the latch is located in the path of the telescopically retractable plunger rod such that it can be impinged thereby and adjusted into the released position.

Here, it is advantageous for the locking latch arranged at the plunger to be adjustable, by a guiding surface connected to the locking latch and a protruding area arranged at the plunger rod, out of its coupling or locked position into the perimeter of the plunger against its return force, which protrusion is arranged at the plunger rod in the proximity of the end facing the hollow needle. This results in a beneficial geometric allocation of the locking latch and its guiding surface in reference to the protruding area at the plunger rod, allowing the unlocking and/or release of the coupling between the plunger and the plunger space, approximately simultaneous to the locking of the plunger rod to the plunger.

It is beneficial for the plunger to be arranged inside the plunger rod which exhibits a hollow profile or a groove-like cross-sectional profile, and the plunger rod receiving the plunger and at least a portion of its ram in its inside prior to the operational position. This leads of a desired space-saving arrangement, in which the length of the ram and the length of the plunger rod are approximately equivalent, but due to one of them being located inside the other, a respectively long arrangement is avoided.

The parts telescopically adjustable in the longitudinal direction in reference to each other, namely the plunger rod and the plunger displaceable in reference thereto, with actually the plunger rod being displaceable in reference to the plunger in the operational position, may comprise snapping connections as mutual locks at several intermediate positions, which result in a coupling between the plunger rod and the plunger in the operational direction of the plunger, which operation of the plunger is blocked or remains blocked by the coupling of the plunger to the plunger space via the locking latch in the intermediate position. When the plunger rod is displaced by an outward retraction from the plunger space in reference to the locked plunger, in particular several positions result in which the plunger rod enters into a form-fitting connection with the plunger effective in the axial direction, which is not suitable to displace the plunger, though, because due to these locks the plunger in turn is coupled to the plunger space in the intermediate position and thus it is locked and remains blocked. In case the user attempts an application with an only partially retracted plunger rod, he/she realizes that it is impossible due to the described locking, and the user is forced to further retract the plunger rod until it has reached its operational position and thus the plunger is unlocked for the operational motion.

The snapping connections can be embodied by ramps or tongues arranged at the interior of the plunger rod, which in turn cooperate with a particularly spring-elastic tongue at the plunger, which tongue can be first compressed by the ramps when the plunger rod is retracted and by its return force it can respectively be moved behind the ramp, particularly in an audible fashion in its locking direction. Such locks formed by ramps and spring-elastic tongues gliding over them are widely known and represent a simple way to allow a potential motion in one direction and blocking it in the opposite direction. When the process of this snapping or blocking is audible, for example by a clicking sound, this snapping process is better indicated to the respective user because he/she can be notified acoustically.

As actually already known from EP 1 323 450 B1, it is particularly advantageous for the plunger rod to be embodied as a grooved part, with the plunger being encompassed and guided in its interior cross-section over a portion of its cross-section, and for the plunger laterally overlapping the free edges of the U-shaped cross-section of the plunger rod via protrusions, which together with the plunger rod fit into the plunger space and fill its interior cross-section, thus they are guided by its interior cross-section. This way, the plunger projects from the cross-sectional form of the U-shaped plunger rod and complements it for a beneficial, rectangular cross-section, which fits into the correspondingly rectangular interior cross-section of the plunger space, with the protrusions of the plunger in reference to the plunger rod can simultaneously be used for its locking to the plunger space.

Here, due to the geometry between the plunger and the plunger rod it is possible that the side of the plunger comprising the locking latch is slotted for separating the locking latch from the lateral area of the plunger and the limit of the slot located outside the plunger rod laterally projects from the plunger by approximately the thickness of the exterior wall of the plunger rod so that at the area located outside the cross-section of the telescopic plunger rod the plunger shows an overall width equivalent to the overall width of the plunger rod and the interior width of the plunger space, which practically represents the syringe chamber.

Overall, a syringe device develops, in which the advantages of the syringe device according to EP 1 323 450 B1 remain upheld, particularly with regard to the space-saving arrangement prior to use and the good fastening of the solid medicaments in a clamping sheath inside the receiving chamber, while simultaneously achieving that the user is forced to retract the plunger rod to such an extent that the coupling between the plunger and the plunger space is released and only then the application of the medicament is possible.

BRIEF DESCRIPTION OF THE DRAWINGS

In the following, an exemplary embodiment of the invention is described in greater detail using the drawing. Shown in a partially schematic illustration is:

FIG. 1 a top view,

FIG. 2 a longitudinal cross-sectional view of a syringe device according to the invention along the line II-II in FIG. 1 in the initial position prior to the retraction of the plunger rod and the release of the plunger, FIG. 3 a cross-sectional view according to FIG. 2, however, in a position rotated by 180° around the longitudinal axis, after the removal of a protective cap and after the telescopic retraction of the plunger rod out of the end of the plunger space facing away from the hollow needle for locking with the plunger, FIG. 4 an opposite view of the syringe device in reference to FIG. 1 after the retraction of the plunger rod into its operational position and the corresponding coupling with the plunger and the release of said plunger in reference to the plunger space, FIG. 5 an illustration according to FIG. 3 after the displacement of the plunger rod and thus also the plunger in the direction of application, resulting in a solid medicament being pushed out of the cannula according to the cross-sectional line V-V in FIG. 6, FIG. 6 a view according to FIG. 4 after the insertion of the plunger rod into the plunger space and thus the advance of the plunger as well as the pushing out of the solid medicament, FIG. 7 a top view of the plunger rod and the plunger only in an initial position according to FIGS. 1 and 2 showing the open side of the plunger rod, groove-shaped or U-shaped in its cross-section, in the initial position according to FIGS. 1 and 2, FIG. 8 a graphic illustration of the arrangement of the plunger, its ram, and the plunger rod only after the retraction of the plunger rod into the position according to FIGS. 3 and 4 without the plunger space receiving said arrangement in the operational position, FIG. 9 a graphic illustration of the arrangement according to FIG. 8 seen from a slightly different angle, FIG. 10 a side view of the arrangement according to FIG. 8 with a view to one U-leg of the plunger rod, having a U-shaped cross-section, after its retraction in reference to the plunger and the impinging of the locking latch of the plunger, by which said plunger was coupled to the plunger housing, not shown in FIGS. 7 to 10, prior to the retraction of the plunger rod, FIG. 11 a partial longitudinal cross-sectional view of the plunger space and the plunger in the locking position with a view to the plunger rod retracted according to FIG. 4, with a detachable locking latch being discernible at the plunger, in the locked position cooperating with the plunger space, FIG. 12 a graphic illustration of the lock of the plunger in reference to the plunger space with the plunger rod being retracted, the plunger and the plunger rod being in the position shown in FIG. 8, FIG. 13 a graphic illustration of the locking of the plunger in reference to the plunger space with a partially or entirely retracted plunger rod in a view off-set by approximately 90° in reference to FIG. 12, and FIG. 14 a side view of the syringe device according to the invention similar to the cross-section of FIG. 3 with a view to the locking of the plunger to the plunger space.

DETAILED DESCRIPTION OF THE PREFERRED EMBODIMENTS

Figure 3:
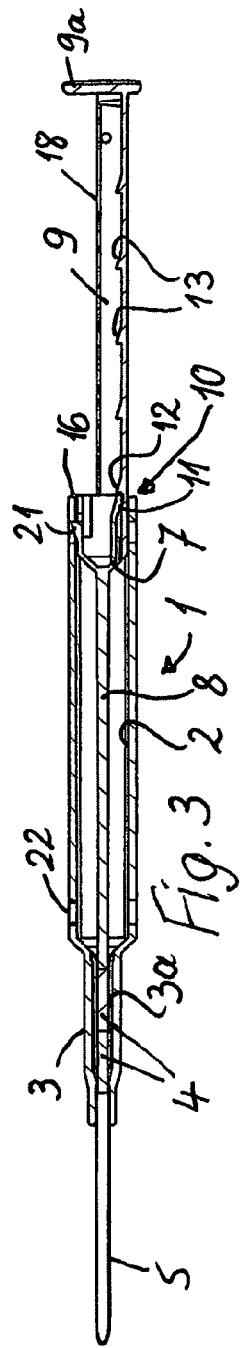

A syringe device, marked 1 in its entirety, comprises in general a structure similar to the device described in EP 1 323 450 B1 and is also used accordingly in practice.

In the drawing it is discernible that the syringe device 1 comprises an oblong, housing-like plunger space 2, which may also be shaped as a cylinder, however showing a rectangular cross-section in the exemplary embodiment, as particularly discernible from the combined analysis of all figures. A receiving chamber 3 is adjacent to the plunger space 2, serving to receive a clamping sheath 3a for one or more solid medicaments 4 contained therein, as discernible in FIGS. 2, 3, 5, and 6.

Additionally, in the extension of the receiving chamber 3, at least when the syringe device 1 is being used, a hollow needle 5 is arranged and connected to the plunger space 2, (through which) after its insertion into an application site the solid medicament 4 can be applied.

In FIGS. 1 and 2 a protective cap 6 is discernible that can cover the hollow needle 5 or which first must be removed in order to allow bringing the hollow needle 5 into its operational position.

Figure 5:
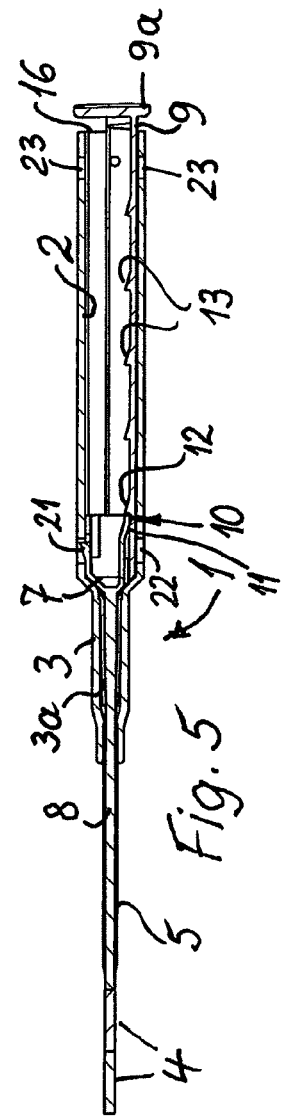

A plunger 7 is provided for pushing the solid medicament or medicaments 4 out of the receiving chamber 3 and through the hollow needle 5 into the plunger space 2, carrying a ram 8 for impinging and pushing the solid medicament 4 through the hollow needle 5 and out of it, with the ram 8 being arranged in the longitudinal direction of the syringe device 1 and in front thereof in the direction of motion of the plunger, as clearly discernible in FIGS. 2, 3, and 5 as well as in FIGS. 7 through 10.

Figure 4:
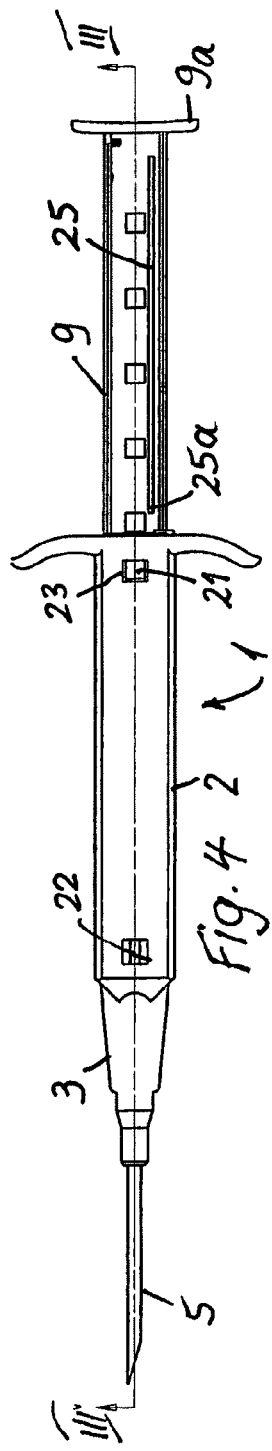

For this motion of the plunger 7 out of its initial position discernible in FIGS. 2 and 3 into the position according to FIGS. 5 through 8, 9, and 10, with said plunger motion causing the above-mentioned pushing out of the solid medicament 4, a plunger rod, in its entirety marked 9 and engaging the plunger 7, is provided having a handle 9a, which for its use can be telescopically extendable and/or first may be extended in reference to the plunger 7 against the operational direction out of the plunger space 2 receiving it, i.e. from the position shown in FIGS. 1 and 2 as well as 7 into the one position shown in FIGS. 3, 4 as well as 8 through 14 and can also be retracted. In this operational position simultaneously a coupling of this telescopic plunger rod 9 to the plunger 7 occurs via a lock 10, in turn comprising on one side a tongue 11 at the plunger 7 and on the other side a ramp-like protrusion 12 at the plunger rod 9.

Figure 6:
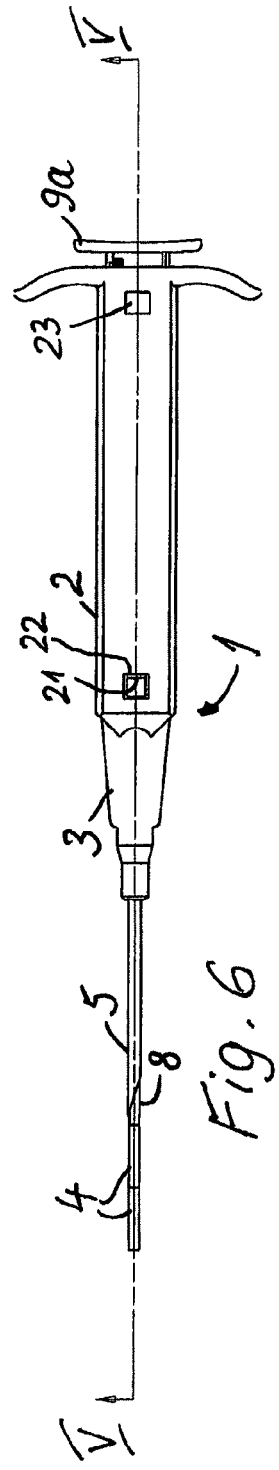

This mutual locking is clearly discernible in FIGS. 8, 11, 12, and also in FIG. 3. When the plunger rod 9 is reinserted into the plunger space 2 the plunger 7 is entrained, as shown in FIGS. 5 and 6, so that its ram 8 arranged in front of it in the travel direction pushes the solid medicament or medicaments 4 out of the hollow needle 5.

Primarily in FIGS. 2 through 5, 7, 8, and 12 it is discernible that the parts or sections of the plunger 7 and primarily of the plunger rod 9 telescopically adjustable in reference to each other comprise several mutual locks or blockages for intermediate positions of the plunger rod 9, extendable in reference to the plunger 7, which locks prevent, when the plunger rod 9 is only partially retracted in reference to the plunger 7, any displacement in the direction of application, i.e. in the drawings from the right to the left. It is discernible primarily in FIGS. 8 and 12 that besides the ramp-like protrusion 12 allocated to the lock 10 additional ramp-like protrusions 13 are provided at the interior bottom of the plunger rod 9 in its progression, which may respectively cooperate with the tongue 11 of the plunger 7 when in an intermediate position between FIGS. 2 and 3 an only partially executed retraction motion of the plunger rod 9 has led to a cooperation of the tongue 11 with one of these ramps 13 in the sense of a blockage.

In order for the retraction of the plunger rod 9 into the plunger housing 2 not leading to a displacement of the plunger 7 in such an intermediate position and the medicament 4 not being pushed out only partially due to an only partial retraction, a coupling or lock 14 of the plunger 7 to the plunger space 2 is provided, particularly shown in FIGS. 11 through 14 and marked 14 in its entirety, which can only be released by the plunger rod 9 being completely retracted into the operational position, in which the plunger rod 9 is connected in the pushing direction to the plunger 7 via the lock 10. This way it is achieved that the plunger 7 is only released from the plunger housing 2 in the pushing direction if the plunger rod 9 is entirely retracted into the position shown in FIGS. 3, 4, and 8 such that the entire displacement path for applying the medicament 4 is also available. Faulty operation by an only partially retracted plunger rod 9 can therefore be avoided.

Primarily in FIGS. 7, 8, and 11 through 14 it is discernible that at the plunger 7, a protrusion 15 is provided, elastic or adjustable to the contour of the plunger 7, which is allocated to the coupling or lock 14 and which engages a coupling recess at a coupling site of the plunger space 2, with the plunger 7 according to FIGS. 2, 7, and 11 through 14 positioned in the initial position and/or the piston 7 being retracted, with the recess 15b, embodied with an open end in the exemplary embodiment, may be formed at the rear edge 16 of the plunger space 2 and allowing the protrusion 15 to insert and snap in, preventing any displacement of the plunger 7 in the direction of application. Here, the above-mentioned figures illustrate that the protrusion 15 arranged at the plunger 7 is a snapping or locking latch, in the coupling position engaging at a point below or behind said position of the plunger space 2 or its housing, namely at the already-mentioned indentation or recess 15b.

Here, the protrusion 15 may comprise at its exterior edge region another small protrusion, pointing in the feeding direction, increasing the compression of said locking latch with the protrusion 15 into the interior of the plunger unless it occurs intentionally by the plunger rod 9 in order to largely exclude any manipulations and also unintended faulty operations.

Therefore, when the plunger rod 9 is retracted out of its initial position according to FIGS. 1 and 2 to such an extent only that the tongue 11 allocated to the lock 10 snaps into one of the ramps 13 the plunger 7 cannot be displaced in the direction of application, because the locking latch allocated to the lock 14 prevents it with its protrusion 15 by it engaging the recess 15b in the plunger space 2.

This locking latch, arranged at the plunger 7 with the protrusion 15 is pivotal or adjustable, on the one side, by a diagonal guiding surface 15a connected to the locking latch, and on the other side, a projecting area 17 arranged at the plunger rod 9 from its coupling or locking position against its retention force into the perimeter of the plunger 7 to such an extent that said lock 14 is released. The above-mentioned projecting area 17 is here located at the plunger rod 9 according to FIGS. 7 through 10 near its end facing the hollow needle 5 so that the plunger rod 9 must actually be retracted to the position in which then simultaneously the locking 10 must occur, in order to bring the locking link allocated to the coupling or lock 14 out of engagement.

Here, a limiting rib 25 is indicated in FIGS. 2, 4, 7, and 11, which extends in the pushing direction next to the ramps 13 inside the plunger rod 9 and ends at a slight distance in front of the forward end of the plunger rod 9, seen in the direction of feed, and prevents any pivoting of the locking latch comprising the protrusion 15 into the interior of the plunger 7 until said front end 25a of said limiting rib 25 has left the plunger area, which is shown in FIGS. 4 and 11. Only in this completely retracted position can the protrusion 15 be pivoted inwardly, while this is prevented in any intermediate position of the plunger rod by the limiting rib 25, so that in an intermediate position no manipulation is possible at the plunger lock.

The user therefore retracts the plunger rod 9 from the position shown in FIGS. 2 and 7 into the position shown in FIGS. 3, 4, and 8 through 14, on the one side bringing the last ramp 12 with the tongue 11 of the lock 10 into the operational contact in the direction of retraction and thus into the operational position, while simultaneously the lock 14 ends its locking function by the protrusion 15 at the locking latch pivoting into the perimeter of the plunger 7. Here, FIGS. 8 and 11 through 14 show, for reasons of greater visibility, the protrusion 15 shortly before its re-pivoting into the interior of the plunger 7, although the plunger rod 9 has already been retracted to such an extent that it is coupled to the plunger 7. However, in reality in this coupling position, in which the plunger rod 9 and the plunger 7 are connected in a form-fitting fashion for a joint pushing motion in the direction towards the cannula 5 and the medicament 4, the lock 14 has already been released in the above-described fashion.

All this is possible because the plunger 7, similar to the device described in EP 1 323 450 B1, is arranged inside the plunger rod 9 provided with a cross-section forming a hollow profile and/or a groove-like profile, and receives the plunger 7 and at least a portion of its ram 8 prior to the retracting of the plunger rod 9 into the operational position in a space-saving manner, which is primarily discernible according to FIGS. 1, 2, and 7. The portion of the plunger rod 9 receiving the plunger 7 can therefore be retracted into the operational position between the plunger 7 and the plunger space 2 in reference to these two parts.

Due to the tongue 11 of the plunger 7 allocated to the lock 10 and the ramp-like diagonal locking protrusions 13 of the plunger rod 9 the parts, telescopically adjustable in the longitudinal direction in reference to each other, namely the plunger rod 9 and the plunger 7, displaceable in reference thereto, which remains fixed during use, though, because the plunger rod 9 performs the displacing motion, therefore comprise snapping connections as mutual locks in several intermediate positions, which as already described cause a coupling between the plunger rod 9 and the plunger 7 in the direction of operation of the plunger 7, which operation of the plunger 7 however remains blocked in such intermediate positions by the coupling of the plunger 7 to the plunger space 2 via the locking latch comprising the protrusion 15. The snapping connections are formed by the ramps or tongues 13 arranged at the interior of the plunger rod 9, which in turn cooperate with the spring-elastic tongue 11 at the plunger 7, which tongue 11 initially being compressible by the ramps 13 when the plunger rod 9 is retracted and then audibly snaps into the locking position behind the respective ramp 13. Here, it is clearly discernible particularly from FIGS. 8 and 12 that the tongue 11 located at the plunger 7 is arranged at a plunger limit extending approximately perpendicular in reference to said plunger limit at which the protrusion 15 for the locking link projects.

When retracting the plunger rod out of its initial position into the operational position, at each contact between the tongue 11 and one of the ramps 13 clicking sounds develop that can catch the attention of the user that corresponding intermediate positions have been reached. After the last clicking sound after which the plunger rod 9 cannot be pulled any further out of the plunger space 2, simultaneously the plunger 7 is unlocked in reference to the plunger space 2 by the reverse pivoting of the locking latch with the protrusion 15 into the interior of the perimeter of the plunger space 2 such that the application process can be performed over the entire feeding length of the plunger rod 9.

From the drawings and primarily from FIGS. 8 and 12 it is discernible that in the exemplary embodiment, the plunger rod 9 is embodied as a groove-like part, with its cross-section being u-shaped and encompassing and guiding the plunger 7 over a portion of its cross-section or perimeter. Here, the plunger 7 laterally overlaps the free edges 18 of this u-shaped cross-section of the plunger rod 9 via protrusions 19 and 20 by an amount approximately equivalent to the dimension or thickness of the walls of the plunger rod 9 such that the plunger 7 also fits into the plunger space 2 outside the plunger rod 9 and is guided by its interior cross-section, as also applicable for the plunger rod 9 and its exterior perimeter. In practice, the plunger 10 with its exterior cross-section complements the exterior cross-section of the plunger rod 9 such that it is approximately matching to the interior cross-section of the plunger space 2 and thus allows the guidance therein in the direction of displacement.

In order for the unit comprising plunger rod 9 and plunger 7 shown in FIG. 7 to fit into the plunger space 7 in two positions reversed by 180°, a recess 22 is provided for, after the application, locking the plunger in the end position with the help of a locking tongue 21 at the plunger space 2 at two opposite positions, which is also equivalent to a respective recess 23 for the initial position of the plunger, in order to receive said tongue 21, displaceable in the direction of application.

In order for the protrusion 15 and the guiding surface 17 comprising the locking latch being mobile in spite of the protrusion 20 arranged thereabove, yet in the area of said locking latch and also the interior the guidance of the plunger 7 with its protrusion 20 being easily possible, the side of the plunger 7 comprising the locking latch is slotted for separating this locking latch from the lateral area of the plunger and in FIGS. 9 and 10, the slot 24 is discernible at the side of the plunger underneath the protrusion 20. The limits of the slot 24 located outside or above the plunger rod 9 is here laterally projecting as the protrusion 20 by approximately one third of the thickness of the lateral wall of the plunger rod 9, so that the plunger 7 at its area located outside of the telescopic plunger rod 9 and/or outside of its cross-section combined with the protrusion 19 arranged at the other side shows an overall width equivalent to the overall width of the plunger rod 9 and the interior width of the plunger space 2, which contributes to a good guidance of the overall arrangement comprising the plunger 7 and the plunger rod 9.

The syringe device 1 comprises an oblong plunger space 2, a receiving chamber 3 for receiving solid medicaments 4, and a hollow needle 5 arranged at the plunger space 2, as well as a plunger 7 suitable for moving in the plunger space 2, carrying a ram 8 for pushing out the solid medicament 4. In the initial position the plunger 7 with the solid medicament 4 is held fixed by a lock in the plunger space 2 as far away as possible. A plunger rod 9 is provided to displace the plunger 7, engaging it, which for its operation can be retracted telescopically out of the plunger space 2 and in reference to the plunger 7, and which can be coupled to the plunger via a lock 10. The lock of the plunger 7 to the plunger space 2 is only opened or released by a complete retraction of the plunger rod 9 into its operational position, while in this position the plunger rod 9 is simultaneously coupled to the plunger 7 in the direction of displacement such that then the medicament can be pushed out. In order to prevent the user from performing any faulty operation by a partial retraction of the plunger rod 9, the plunger 7 and the plunger rod 9 comprise at least one or more mutual locks for intermediate positions, in which the plunger 7 is still locked to the plunger space 2.

The invention claimed is:

1. A syringe device (1) comprising:
an oblong plunger space (2), having a receiving chamber (3) for receiving one or more solid medicaments (4);
a hollow needle (5) arranged at the plunger space (2);
a plunger (7) suitable for movement in the plunger space (2), the plunger (7) including a ram (8) for pushing out the solid medicament (4) through and out of the hollow needle (5), and the plunger included a lock (14) which couples the plunger (7) to the plunger space (2);
a plunger rod (9) coupled to the plunger (7);
wherein the plunger rod (9) is at least one of telescopically extendable or retractable in reference to the plunger space (2) and to the plunger (7);
wherein parts of the plunger (7) and the plunger rod (9) are telescopically adjustable in reference to each other and include one or more mutual locks at intermediate positions of the plunger rod (9) that are retractable in reference to the plunger (7), wherein the one or more mutual locks prevent displacement of the plunger (7) towards the hollow needle (5) when the plunger rod (9) is only partially retracted;
wherein the lock (14) is releasable by the plunger rod (9) being completely retracted to an operational position;
wherein, when the lock (14) is released, the one or more mutual locks do not prevent displacement of the plunger (7) towards the hollow needle (5) and the plunger (7) is displaceable in the direction of the hollow needle (5) to push the solid medicament (4) through and out of the hollow needle (5); and
wherein the plunger (7) is arranged inside the plunger rod (9) which forms a hollow profile or comprises a groove-shaped cross-sectional profile, and receives the plunger (7) and at least a portion of the ram (8) prior to attaining the operational position.

2. A syringe device according to claim 1, wherein the plunger includes an elastic or adjustable protrusion (15) (7) that is adjustable into a perimeter of the plunger (7), which automatically engages a coupling recess or hole (15*b*) at a coupling site of the plunger space (2) when the plunger (7) is retracted.

3. A syringe device according to claim 2, wherein the protrusion (15) on the plunger (7) is a snapping or locking latch, and in a coupling position engages the plunger space (2) at a position underneath the plunger space (2).

4. A syringe device according to claim 3, wherein the locking latch on the plunger (7) is adjustable by a guiding surface (15*a*) connected to the locking latch and a protrusion area (17) arranged on the plunger rod (9) from a coupling or locked position into the perimeter of the plunger (7) against a retraction force, the protrusion area (17) being arranged on the plunger rod (9) near an end facing the hollow needle (5).

5. A syringe device according to claim 1, wherein the plunger rod (9) and the plunger (7) comprise snapping connections as the mutual locks at several of the intermediate positions, causing a coupling of the plunger rod (9) and the plunger (7) in a direction of operation of the plunger (7), with an operation of the plunger (7) in the intermediate positions being blocked by the coupling of the plunger (7) to the plunger space (2) via the lock (14).

6. A syringe device according to claim 5, wherein the snapping connections are formed by the ramps or tongues (13) arranged on an interior of the plunger rod (9), which in turn cooperate with a spring-elastic tongue (11) on the plunger (7), the tongue (11) is initially compressible by the ramps (13) when the plunger rod (9) is retracted, and can be moved into a locking position behind the ramp (13) by a retraction force.

7. A syringe device according to claim 1, wherein the plunger rod (9) is embodied U-shaped in an interior cross-section, and the plunger (7) is encompassed and guided over a part of its cross-section therein, and the plunger (7) laterally overlaps free edges (18) of the U-shaped cross-section of the plunger (9) via protrusions (19, 20), which fit together with the plunger rod into the plunger space (2) and are guided by the interior cross-section.

8. A syringe device according to claim 1, wherein a side of the plunger (7) comprising the locking latch includes a slot for separating the locking latch from the lateral side of the plunger and a limit of said slot (24) is located outside the plunger rod (9) and projects from the plunger by approximately a thickness of a lateral wall of the plunger rod (9) such that the plunger at an area thereof located outside the telescopic plunger rod (9) has an overall width equivalent to an overall width of the plunger rod (9) and an interior width of the plunger space (2).

* * * * *